United States Patent
Ferguson et al.

(10) Patent No.: US 6,696,433 B2
(45) Date of Patent: Feb. 24, 2004

(54) USE OF SEX STEROIDS FUNCTION MODULATORS TO TREAT WOUNDS AND FIBROTIC DISORDERS

(75) Inventors: Mark W J Ferguson, Derbyshire (GB); Gillian S Ashcroft, Wigan (GB)

(73) Assignee: Renovo Limited, Manchester (GB)

( * ) Notice: Subject to any disclaimer, the term of this patent is extended or adjusted under 35 U.S.C. 154(b) by 0 days.

(21) Appl. No.: 09/939,611

(22) Filed: Aug. 28, 2001

(65) Prior Publication Data

US 2002/0042401 A1 Apr. 11, 2002

Related U.S. Application Data

(63) Continuation of application No. 09/230,226, filed as application No. PCT/GB97/01973 on Jul. 22, 1997, now abandoned.

(30) Foreign Application Priority Data

Jul. 22, 1996 (GB) ............................................. 9615348
Jan. 27, 1997 (GB) ............................................. 9701600

(51) Int. Cl.$^7$ ........................ A61K 31/565; A61P 17/02
(52) U.S. Cl. ........................................ 514/182; 514/928
(58) Field of Search ................................ 514/874, 886, 514/928, 182

(56) References Cited

U.S. PATENT DOCUMENTS

| | | | |
|---|---|---|---|
| 4,150,128 A | 4/1979 | Jasionowski | |
| 4,642,305 A | 2/1987 | Johansson et al. | |
| 4,684,635 A | 8/1987 | Orentreich et al. | |

FOREIGN PATENT DOCUMENTS

| | | |
|---|---|---|
| EP | 0 435 200 | 7/1991 |
| GB | 2 109 231 | 6/1983 |
| GB | 2 167 296 | 5/1986 |
| GB | 2 167 957 | 6/1986 |
| WO | WO 85/00519 | 2/1985 |
| WO | WO 93/10141 | 5/1993 |
| WO | WO 94/02130 | 2/1994 |
| WO | WO 94/17839 | 8/1994 |
| WO | WO 95/32709 | 12/1995 |
| WO | WO 97/41867 | 11/1997 |

OTHER PUBLICATIONS

Morales et al.; Estrogen Promotes Angiogenic Activity in Human Umbilical Vein Endothelial Cells in Vitro and in A Murine Model; 1995, Circulation, vol. 91, No. 3, pp. 755–763.*
Nandi et al.; Role of Anabolic Steriod in Clean Surgical Wounds, 1986, J. Indian Med. Assoc., vol. 84, No. 4, pp. 116–118.*
Nair et al.; Effect of Anabolic Steroid on Experimental Wound Healing in Calves, 1997, Ind. J. Vet. Surg., vol. 18, No. 1, pp. 15–16.*
Jaworski; The Effect of Estradiol Upon Healing of Wounds of The Urinary Bladder in The Guinea Pig, 1973, Elsevier Science Pub. Amsterdam, Abstract.*
Schmidt et al, "New Treatment of Atrophic Acne Scars by Iontophoresis With Estriol and Tretnoin", International Journal of Dermatology 34(1):53–57 (1995).
Pirk et al, "Effect of analogues of steroid and thyroxine hormones on wound healing in hamsters", J. Periodontal Res. 9:290–297 (1974).

(List continued on next page.)

*Primary Examiner*—Edward J. Webman
(74) *Attorney, Agent, or Firm*—Nixon & Vanderhye P.C.

(57) ABSTRACT

The present application relates to the use of compounds that influence the sex hormone system for the treatment of wounds and/or fibrotic disorders. Preferred compounds for use in such treatments are steroid hormones and especially the oestrogens.

9 Claims, 6 Drawing Sheets

OTHER PUBLICATIONS

Santos–Pinto et al, "Pharmacological Effect of Nandrolone Phenylpropionate on the Healing of Dental Extraction Wounds" A Histological Investigation in Rats, J. Nihon Univ. Sch. Dent. 12(2):57–61 (1970).

Schmidt et al, "New Treatment of Atrophic Acne Scars by Iontophoresis With Estriol and Tretinoin", International Journal of Dermatology 34(1):53–57 (1995).

Pirk et al, "Effect of analogues of steroid and thyroxine hormones on wound healing in hamsters", J. Periodontal Rs. 9:290–297 (1974).

Shah et al, "Neutralising antibody to TGF-$\beta_{1,2}$ reduces cutaneous scarring in adult rodents", Journal of Cell Science 107:1137–1157 (1994).

Bloch et al, "The angiogenesis inhibitor endostatin impairs blood vessel maturation during wound healing", The FASEB Journal 14(15):2373–2376 (2000).

Berger et al, "The Angiogenesis Inhibitor, Endostatin, Does Not Affect Murine Cutaneous Wound Healing", Journal of Surgical Research 91:26–31 (2000).

Jang et al, "Role of $\alpha_v$ integrins and angiogenesis during wound repair", Wound Rep. Reg. 7:375–380 (1999).

Jang et al, "Vitronectin deficiency is associated with increased wound fibrinolysis and decreased microvascular angiogenesis in mice", Surgery 127(6):696–704 (2000).

Shah et al, "Neutralisation of TGF-$\beta$1 and TGF-$\beta$2 or exogenous addition of TGF-$\beta$3 to cutaneous rat wounds reduces scarring", Journal of Cell Science 108 (Pt 3): 985–1002 (1995).

Murthy et al, "Effects of estrogen on wound healing—An Experimental Study", Indian Journal of Surgery 36(1):1–7 (1974).

Lundgren, "Influence of Estrogen and Progesterone on Vascularization of Granulation Tissue in Preformed Cavities", Scand. J. Plast. Reconstr. Surg. 7:85–90 (1973).

Lundgren, "Influence of Estrogen and Progesterone on Exudation, Inflammatory Cell Migration and Granulation Tissue Formation in Preformed Cavities", Scand. J. Plast. Resconstr. Surg. 7:10–14 (1973).

Hertsler, Wound Healing (The Formation of Fibrous Tissue), The Peritoneum vol. 1, Chapter V, Mosby St. Louis (1919).

Jaworski, "The effect of estradiol upon healing of wounds of the urinary bladder in the guinea pig", Elsevier Science, accession No. 279680 (1973).

Morales et al, "Estrogen promotes angiogenic activity in human umbilical vein endothelial cells in vitro and in a murine model", Circulation 91(3):755–763 (1995).

Nandi et al, "Role of anabolic steroid in clean surgical wounds", J. Indian Med. Assoc. 84(4):116–118 (1986).

Maghuin–Rogister, J. Pharm. belg. 50(5):455–460 (1995)—abstract only.

Yamaguchi et al, Calcif. Tissue Int. 60(6):527–532 (1997)—abstract only.

Terada et al, Jpn. J. Toxicol. Environ. Health 38(6) (1992)—abstract only.

* cited by examiner

USE OF SEX STEROIDS FUNCTION MODULATORS TO TREAT WOUNDS AND FIBROTIC DISORDERS

This application is a continuation of Application Ser. No. 09/230,226, filed Apr. 21, 1999, which is a 371 of PCT/GB97/01973, filed Jul. 22, 1997, the entire content of which is hereby incorporated by reference in this application.

The present invention relates to wound healing and also to regulating fibrosis in the treatment of conditions in which fibrosis is a major mechanism of tissue repair or where excessive fibrosis leads to pathological derangement and malfunctioning of tissue.

Wound healing in adults is a complicated reparative process. The healing process begins with the recruitment of a variety of specialised cells to the site of the wound and involves extracellular matrix and basement membrane deposition, angiogenesis, selective protease activity and re-epithelialisation. An important component of the healing process in adult mammals is the stimulation of fibroblasts to generate the extracellular matrix. This extracellular matrix constitutes a major component of the connective tissue which develops to repair the wound area.

The connective tissue that forms during the healing process is often fibrous in nature and commonly forms into a connective tissue scar (a process known as fibrosis).

A scar is an abnormal morphological structure resulting from a previous injury or wound (e.g. an incision, excision or trauma). Scars are composed of a connective tissue which is predominately a matrix of collagen types 1 and 3 and fibronectin. The scar may consist of collagen fibres in an abnormal organisation (as seen in scars of the skin) or it may be an abnormal accumulation of connective tissue (as seen in scars of the central nervous system). Most scars consist of abnormally organised collagen and also excess collagen. In man, in the skin, scars may be depressed below the surface or elevated above the surface of the skin. Hypertrophic scars are a more severe form of normal scarring, are elevated above the normal surface of the skin and contain excessive collagen arranged in an abnormal pattern. A keloid is another form of pathological scarring which is not only elevated above the surface of the skin but also extends beyond the boundaries of the original injury. In a keloid there is excessive connective tissue which is organised in an abnormal fashion predominately in whirls of collagenous tissue. There are genetic predispositions to forming both hypertrophic scars and keloids. They are particularly common in Africo-Carribean and Mongoloid races.

There is a need to provide medicaments that promote the healing of wounds. For example, it is often desirable to increase the rate of healing in the case of acute wounds (such as penetrative injuries, burns, nerve damage or even wounds resulting from elective surgery), chronic wounds (such as diabetic, venous and decubitus ulceration) or for generally healing compromised individuals (for example the elderly). In these examples, the wounds can severely influence quality of life or even result in death and therefore the rate of healing often needs to be increased as much as is clinically possible. Where the rate of wound healing is increased, there is often an associated increase in scar formation but this may be of secondary importance compared to the desired increase in the rate of healing.

The term "wound" as used herein is exemplified but not limited to injuries to the skin. Other types of wound can involve damage, injury or trauma to an internal tissue or organ such as the lung, kidney, heart, gut, tendons or liver.

There are however other instances where the regulation of scar formation is of primary importance and the rate of wound healing is only of secondary consideration. Examples of such situations are scars of the skin where excessive scarring may be detrimental to tissue function and particularly when scar contracture occurs (for instance skin burns and wounds which impair flexibility of a joint). The reduction of scarring to the skin when cosmetic considerations are important is also highly desirable. In the skin, hypertrophic or keloid scars (particularly in Africo-Caribbean and Mongoloid races) can cause functional and cosmetic impairment and there is a need to prevent their occurrence. Scarring resulting from skin grafts in both donor sites and from the application of artificial skin can also be problematic and need to be minimised or prevented.

As well as scars of the skin, internal scarring or fibrosis can be highly detrimental and specific examples include:

(i) Within the central nervous system, glial scarring can prevent neuronal reconnection (e.g. following neurosurgery or penetrating injuries of the brain).

(ii) Scarring in the eye can be detrimental. In the cornea, scarring can result in abnormal opacity and lead to problems with vision or even blindness. In the retina, scarring can cause buckling or retinal detachment and consequently blindness. Scarring following wound healing in operations to relieve pressure in glaucoma (e.g. glaucoma filtration surgery) results in the failure of the surgery whereby the aqueous humour fails to drain and hence the glaucoma returns.

(iii) Scarring in the heart (e.g. following surgery or myocardial infarction) can give rise to abnormal cardiac function.

(iv) Operations involving the abdomen or pelvis, often result in adhesion between viscera. For instance, adhesions between elements of the gut and the body wall may form and cause twisting in the bowel loop leading to ischaemia, gangrene and the necessity for emergency treatment (untreated they may even be fatal). Likewise, trauma or incisions to the guts can lead to scarring and scar contracture to strictures which cause occlusion of the lumen of the guts which again can be life threatening.

(v) Scarring in the pelvis in the region of the fallopian tubes can lead to infertility.

(vi) Scarring following injury to muscles can result in abnormal contraction and hence poor muscular function.

(vii) Scarring or fibrosis following injury to tendons and ligaments can result in serious loss of function.

Related to the above is the fact that there are a number of medical conditions known as fibrotic disorders in which excessive fibrosis leads to pathological derangement and malfunctioning of tissue. Fibrotic disorders are characterised by the accumulation of fibrous tissue (predominately collagens) in an abnormal fashion within the tissue. Accumulation of such fibrous tissues may result from a variety of disease processes. These diseases do not necessarily have to be caused by surgery, traumatic injury or wounding. Fibrotic disorders are usually chronic. Examples of fibrotic disorders include cirrhosis of the liver, liver fibrosis, glomerulonephritis, pulmonary fibrosis, sclerodermia, myocardial fibrosis, fibrosis following myocardial infarction, central nervous system fibrosis following a stroke or neurodegenerative disorders (e.g. Alzheimer's Disease), proliferative vitreoretinopathy (PVR) and arthritis. There is therefore also a need for medicaments which may be used for the treatment of such conditions by regulating (i.e. preventing, inhibiting, or reversing) fibrosis/scarring in these fibrotic disorders.

Whilst the above considerations mainly apply to conditions, disorders or diseases of man it will be appreciated that wound healing, scarring and fibrotic disorders can also be problematic in other animals, particularly veterinary or domestic animals (e.g. horses, cattle, dogs, cats etc). For instance abdominal wounds or adhesions are a major reason for having to put down horses (particularly race horses), as are tendon and ligament damage leading to scarring or fibrosis.

There have been several recent developments in the fields of wound healing, scarring and fibrotic disorders. Some of these developments revolve around the recent understanding that an array of cytokines and growth factors are intimately involved in the repair of tissues.

WO-A-92/17206 discloses the use of neutralising agents for fibrosis promoting growth factors that may be used to inhibit scar formation during wound healing. For instance, WO-A-92/17206 demonstrates that compositions which specifically inhibit the activity of Transforming Growth Factors β1 and β2 and Platelet Derived Growth Factor are particularly beneficial for reducing scar formation.

WO-A-93/19769 discloses the use of non-fibrotic growth factors, such as Transforming Growth Factors β3 which was surprisingly found to promote healing of a wound without inducing fibrosis.

GB-A-2,288,118 discloses the use of specific antibodies generated against growth factors that improve healing by potentiating the actions of said growth factors.

Another development involves the use of mannose-6-phosphate for use in treating fibrotic disorders associated with accumulation of extracellular matrix and with elevated levels of Transforming Growth Factors β1 or β2 (GB-A-2, 265,310). Mannose-6-phosphate is believed to interfere with the conversion of latent forms of these Transforming Growth Factors into their active form.

Other compositions that influence growth factor efficacy and promote wound healing are disclosed in WO-A-95/26203.

Despite these advances there remains a need to continue to develop medicaments that may be used to modulate the healing of wounds.

According to a first aspect of the present invention, there is provided the use of a compound that influences the sex hormone system for the manufacture of a medicament for the treatment of wounds or fibrotic disorders.

According to a second aspect of the present invention, there is provided a method of treating wounds or fibrotic disorders comprising providing at the site of the wound or fibrotic disorder a therapeutically effective amount of a compound which influences the sex hormone system.

According to a third aspect of the present invention there is provided a healing composition which comprises an amount of a compound that influences the sex hormone system which is therapeutically effective for treating wounds or fibrotic disorders and a pharmaceutically acceptable vehicle.

By "sex hormone system" it is meant the endocrine system that influences gender, sexual development, fertility, secondary sexual characteristics and in females the menstrual cycle and pregnancy. Compounds which are useful are those which have an influence on this system. Examples of such compounds are endogenous hormones such as oestrogens, androgens, progesterone, chorionic gonadotrophin, follicle stimulating hormone and luteinising hormone as well as precursors thereof.

In accordance with the invention, the inventors have established that compounds which influence the sex hormone system may be used for the treatment of wounds and fibrotic disorders. Depending on the compound used, various regulating effects may be provided for the treatment of wounds or fibrotic disorders and these are discussed more fully below.

The invention has been based on our studies which have shown that the rate of wound healing declines with the age of subject in terms of re-epithelialisation, extracellular matrix and basement membrane deposition. We also noticed that aged females heal more quickly than aged males. In females this was associated with aa increased number of wound fibroblasts. Transforming Growth Factor β1 (TGF-β1) levels and increased proteolytic activity compared to aged males but decreased compared to young males and females. It was also noticed that in young males there is less scarring compared to that seen in young females which we associate with differences between TGF-β1 levels observed in the two sexes. Another difference between the sexes was that healing of wounds in females is generally associated with greater levels of elastin and angiogenesis than in males.

These findings led us to the realisation that sex hormones and other compounds which influence the sex hormone system have an influence on the rate and quality (extent of scar formation or fibrosis) of wound healing and also influence fibrous tissue deposition in fibrotic disorders. This hypothesis was examined and confirmed by assessing the effect of Hormone Replacement Therapy (HRT) on the rate and quality of wound healing in post-menopausal women. Women taking HRT of oestrogen alone or oestrogen and progesterone had significantly increased rates of skin wound healing (in terms of re-epithelialisation and extracellular matrix deposition) compared to age-matched women not on medication. Proteolytic activity both in normal (uninjured) skin and in the wounds of the post-menopausal women on HRT was reduced to that of a 20–30 year female age group. These effects were also associated with reversal of age related changes in the transforming growth factor β1 or interleukin-1 profiles in normal skin.

Although the inventors do not wish to be constrained by any hypothesis, they believe it is possible that the mechanism by which the sex hormones and other compounds which influence the sex hormone system exert their wound healing effect is by modulating the activity of molecules which regulate wound heating such as the cytokines (e.g. TGF-β1, Platelet Derived Growth Factor or interleukin-1) and thereby influence cellular function (for example the function of fibroblasts). For instance, our in vitro studies have established that oestrogen increases fibroblast TGF-β production which may be associated with the effect of the oestrogens to cause an increase in the rate of wound healing. Other compounds which influence the sex hormone system also modulate fibroblast activity. For example progesterone inhibits the proliferation of aged fibroblasts whereas androgens have similar effects to those of the oestrogens.

We have found that compounds which influence the sex hormone system also modulate enzyme profiles in a wound or tissue affected by a fibrotic disorder. In particular we have found that enzyme levels of matrix metalloproteinases (MMPs) (especially MMP2 and MMP9) as well as other lytic enzymes such as elastases are modulated by compounds such as oestrogen, progesterone and testosterone. We believe this modulation is sufficient to influence the rate of wound healing or to modulate fibrosis (and thereby influence scarring or fibrotic disorders) and it is possible that these effects represent a complementary, additional or even alternative mechanism (to that discussed in the preceding paragraph) by which compounds which influence the sex hormone system are able to treat wounds or fibrotic disorders.

Several classes of compound are capable of influencing the sex hormone system. Such compounds include hormones, hormone receptor agonists or antagonists, agents which modulate the release of endogenous activators or inhibitors of hormone receptors, agents which modulate the synthesis of endogenous hormone receptors ligand, agents which modulate the breakdown of endogenous hormone receptors ligand, agents which modulate hormone receptor expression or activity and agents which enhance the mechanisms involved in signal transduction between the receptor of the sex hormone system and effector systems.

Preferred compounds which influence the sex hormone system are hormones (or biologically active derivatives thereof) and agonists and antagonists of hormonal receptors. It is most preferred that the compound is a steroid sex hormone (such as oestrogen, progesterone or testosterone) or an agonist or antagonist of sex steroid hormonal receptors.

Compounds which influence the sex hormone system have been found, in accordance with the present invention, to regulate wound healing in one of two principal ways (depending on the particular compound used). These ways are described below with reference to the first and second embodiments of the invention.

In accordance with the first embodiment of the invention, we have established that certain compounds which influence the sex hormone system are capable of accelerating the rate at which a wound heals, although this may be at the expense of providing increased scarring or fibrosis. Such compounds are obviously particularly useful where speed of wound healing is a priority and the quality of any scar is a secondary consideration. Thus such compounds will be useful for acute wounds (such as penetrative injuries, burns, nerve damage, damaged ligaments or tendons, or even wounds resulting from elective surgery) and chronic wounds (such as diabetic, venous and decubitus ulceration). Such wounds can severely influence quality of life or even result in death and therefore the rate of healing may need to be increased as much as is clinically possible.

The compounds which are most effective in accordance with the first embodiment of the invention are generally those which promote oestrogenic activity at the site of the wound. It is this promotion which accelerates the wound healing.

Examples of compounds which may be used to promote oestrogenic activity include oestrogens, oestrogen receptor agonists (such as ethinylyoestradiol, dienoestrol, mestranol, oestradiol, oestriol, conjugated oestrogens, piperazine oestrone sulphate, stilboestrol, fosfesterol tetrasodium, polyestradial phosphate, tibolone), inhibitors of oestrogen or oestrogen receptor agonist breakdown, phytoestrogens or even modulators of luteinising hormone, follicle stimulating hormone and chorionic gonadotrophin.

As an alternative to a promoter of oestrogenic activity, it is possible in accordance with the first embodiment of the invention, to use promoters of androgenic activity.

Preferred promoters of androgenic activity include androgen hormones (such as testosterone, dihydrotestosterone, 5α-androstanediol), androgen receptor agonists (such as testosterone undecanoate, testosterone enanthate, testosterone esters, testosterone proprionate, mesterolone, danazol and gestrinone), inhibitors of androgen or androgen receptor agonist breakdown (such as aminoglutethamide), modulators of luteinising hormone and follicle stimulating hormone, anabolic steroids (such as nandrolone or stanozolol).

The preferred compound for use in the first embodiment of the invention is an oestrogen hormone receptor agonist. 17 β-oestradiol is particularly preferred.

In accordance with the second embodiment of the invention we have established that certain compounds which are capable of influencing the sex hormone system are capable of regulating wound healing or fibrotic disorders by improving the quality of scar formation or preventing inappropriate fibrosis, although possibly at the expense of the rate of wound healing.

Thus such compounds (which inhibit fibrosis) used according to the second embodiment of the invention are useful in situations or conditions where scarring needs to be prevented or reduced such as:

(i) where scars of the skin may be excessive and/or detrimental to tissue function and particularly when scar contracture occurs or may occur (for instance skin burns and wounds which impair flexibility of a joint and particularly scarring in children);

(ii) scarring to the skin when cosmetic considerations are important;

(iii) when hypertrophic or keloid scars (particularly in Africo-Caribbean and Mongoloid races) may occur which can cause functional and cosmetic impairment;

(iv) scarring resulting from skin grafts in both donor sites and from the application of artificial skin;

(v) scarring within the central nervous system (e.g. following neuro-surgery or penetrating injuries of the brain), for example glial scarring can prevent reconnection of severed neurons;

(vi) scarring in the eye and particularly of the cornea (scarring can result in abnormal opacity and lead to problems with vision or even blindness), in the retina (scarring can cause buckling or retinal detachment and consequently blindness) and scarring following wound healing in operations to relieve pressure in glaucoma (e.g. glaucoma filtration surgery) which can result in the failure of the surgery whereby the aqueous humour fails to drain and hence the glaucoma returns;

(vii) scarring in the heart (e.g. following surgery or myocardial infarction) which can give rise to abnormal cardiac function;

(viii) scarring of the gut such as may occur following operations involving the abdomen or pelvis that result in adhesion between viscera (adhesions between elements of the gut and the body wall can form and cause twisting in the bowel loop leading to ischaemia, gangrene and the necessity for emergency treatment—untreated they may even be fatal); likewise, trauma or incisions to the guts can lead to scarring and scar contracture or strictures which cause occlusion of the lumen of the guts which again can be life threatening;

(ix) scarring in the pelvis in the region of the fallopian tubes which can lead to infertility;

(x) scarring following injury to muscles which can result in abnormal contraction and hence poor muscular function;

(xi) scarring or fibrosis following injury to tendons and ligaments which can result in serious loss of function.

Compounds (which inhibit fibrosis) used according to the second embodiment of the invention are also useful for the treatment or prevention of fibrotic disorders such as cirrhosis of the liver, liver fibrosis, glomerulonephritis, pulmonary fibrosis, scleroderma, myocardial hibernation, fibrosis following myocardial infarction, central nervous system fibrosis following a stroke or neuro-degenerative disorders (e.g. Alzheimer's Disease), proliferative vitreoretinopathy (PVR) and arthritis.

Examples of compounds for use in accordance with the second embodiment of the invention include promoters of progesterone activity such as progesterone and other progesterone receptor agonists (such as allyoestrenol, desogestrel, dydrogesterone, ethynodiol diacetate, gestodene, gestranol hexatioate, hydroxyprogesterone hexanoate, levonorgestrel, megestrol acetate, medroxyprogesterone acetate, norethisterone, norethisterone acetate, norethisterone enanthate, norgestimate or norgesterel), inhibitors of progesterone or progesterone receptor agonist breakdown and modulators of luteinising hormone and/or follicle stimulating hormone.

Alternatively, the compound used in the second embodiment of the invention may be an inhibitor of oestrogenic activity. Preferred inhibitors of oestrogenic activity include oestrogen receptor antagonists (such as tamoxifen, clomiphene citrate or cyclofenil), inhibitors of oestrogen production (such as anastrozole, 4-hydroxy androstenedione, exemestane, oestrone-3-O-sulphate, fadrazole hydrochloride or formestane) and phytoestrogens. Tamoxifen is particularly useful for use according to the second embodiment of the invention.

As a further possibility, the compound used in the second embodiment of the invention may be an inhibitor of androgenic activity. Preferred inhibitors of androgenic activity include androgen receptor antagonists (such as cyproterone acetate or flutamide) and inhibitors of androgen production.

Other compounds which influence the sex hormone system may be used according to either the first or second embodiments of the invention. For instance precursors of sex hormones which are subsequently converted to the active compound may be used. Dehydroepiandrosterone (DHEA) and its sulphate ester. DHEA sulphate (DHEAS) and analogues thereof are precursors of oestrogens and androgens and may be used as compounds which influence the sex hormone system according to the first embodiment of the invention to promote the rate of wound healing. We were lead to investigating how efficacious DHEA and DHEAS and analogues thereof may be for modulating wound healing after observing that circulating levels of DHEA and DHEAS decline progressively and markedly with age (which we in turn correlated with slower wound healing), in distinct contrast to other steroids such as glucocorticoids, whose serum levels remain relatively well-preserved with age. We have conducted studies that demonstrate that supplementation of individuals with DHEA (as a precursor of androgens and oestrogen), influences wound healing in the aged by stimulating the rate of wound repair. Therefore DHEA or DHEAS and analogues thereof may be used according to the first embodiment of the invention to promote wound healing.

It will be appreciated that combinations of the above-described compounds may be used to maximise efficacy of the medicament, For instance, a progesterone receptor agonist and an oestrogen receptor antagonist may be combined to maximise the effect on scarring and/or a fibrotic condition.

Other preferred combinations are ones that are effective for treating wounds such that the rate of healing is increased and fibrosis is also inhibited. A combination of an oestrogen receptor agonist and a progesterone receptor agonist may be used for this purpose.

Alternatively compounds of the invention may be given sequentially. For instance an oestrogen agonist may be given pre-operatively (or peri-operatively) to promote the healing of a subsequent surgical incision. Later, while a patient is recovering from the surgery, a progesterone agonist may be given to reduce scarring.

Preferred treatment regimes contemplated by the present invention are non-systemic treatments since systemic application of compounds influencing the sex endocrine system may have undesirable effects, such as influencing secondary sexual characteristics whereas non-systemic administration (e.g. topical application to the skin) only has a local action and therefore does not have such undesirable effects. However, there are cases (for example severe injury or when acute therapy is required) where systemic applications are useful.

The compositions of the invention may take a number of different forms depending, in particular on the manner in which the composition is to be used. Thus, for example, the composition may be in the form of a liquid, ointment, cream, gel, hydrogel, powder or aerosol, It will be appreciated that the vehicle of the composition of the invention should be one which is well tolerated by the patient and allows release of the active compound to the wound. Such a vehicle is preferably biodegradeable, bioresolveable and/or non-inflammatory.

When the compound is a steroid (such as the oestrogens, progesterone, androgens or DHEA) the vehicle may contain a carrier molecule which improves the aqueous solubility of the compound. A suitable carrier is 2-hydroxypropyl-$\beta$-cyclodextrin which is preferably present in the composition in approximately equimolar concentrations to that of the steroid.

The composition of the invention may be used in a number of ways. Thus, for example, a composition in accordance with the first or second embodiment of the invention may be applied in and/or around a wound of a patient to provide the desired regulation of wound healing.

If the composition is to be applied directly to an actual wound, trauma or injury, then the pharmaceutically acceptable vehicle will be one which does not cause an inflammatory response or is toxic to the tissue.

It is however also possible to use compositions in accordance with the invention as a prophylactic, For instance, prior to surgery (particularly elective surgery) it may be desirable to provide a compound which influences the sex hormone system for regulation of healing of the subsequently formed surgical wound so as to increase the rate of wound healing (according to the first embodiment of the invention) or to reduce scarring and/or tract a fibrotic disorder (according to the second embodiment of the invention) as appropriate. In this case the vehicle of the composition will need to be one capable of delivering the compound to the target site. For example the vehicle may need to be suitable for carrying the compound across the keratinous layer of the skin. Examples of suitable vehicles for this purpose include dimethyl sulphoxide and acetic acid.

Composition may be provided on a sterile dressing or patch which may be used to cover or even pack a wound to be treated. In this respect conventional Hormone Replacement Therapy patches may be suitably used for treating wounds and/or fibrotic disorders.

A further important application of the composition of the invention relates to wound healing in the eye. For example, compositions in accordance with the first embodiment of the invention may be used to provide scarring (as well as increase the rate of healing) between the sclera and retina when it is desired to repair a tear in the latter. In this case, the composition of the invention may be an injectable solution. Alternatively, a composition in accordance with the second embodiment of the invention may be used to reduce or control scarring resulting from surgical operations on the eye, e.g. laser surgery on the cornea. In this case, the composition of the invention may be in the form of an eye drop.

Compositions in accordance with the invention may be used in a range of internal wound healing applications (in addition to that mentioned above for the eye). Thus for example, the composition may be formulated for inhalation for use in wound healing of the lungs or for the prevention or treatment of fibrosis and strictures in the lung.

It will be appreciated that the amount of compound that influences the sex hormone endocrine system to be incorporated in a composition in accordance with the invention and/or the amount of the compound to be applied to the wound site depends on a number of factors such as the biological activity and bioavailability of the compound, which in turn depends on the mode of administration and the physicochemical properties of the compound, Other factors include:

A) The half-life of the compound in the subject being treated.
B) The specific condition to be treated.
C) Whether quick healing or reduced scarring is desired.
D) The age of the subject.
E) The sex of the subject.

The frequency of administration will also be influenced by the above mentioned factors and particularly the half-life of the compound within the subject being treated.

Generally when the compositions are used to treat existing wounds or fibrotic disorders the compound should be administered as soon as the wound has occurred or the disorder has been diagnosed. Therapy with the composition should continue until the wound has healed to a clinicians satisfaction or, in the case of a fibrotic disorder, the risk or cause of abnormal fibrous tissue formation has been removed.

Compositions which promote the rate of wound healing according to the first embodiment of the invention should he applied to a wound as soon as possible after the wound has formed. For acute wounds and wounds of subjects who are healing competent (e.g. the young) application of the composition will ideally be at the time of wounding, preferably within hours of wounding and no longer than a few days post-wounding. For chronic wounds or wounds in the healing compromised (e.g. the elderly) administration should be as soon as possible.

Compositions which modulate scarring and/or fibrotic disorders according to the second embodiment of the invention should also be applied to a wound as soon as possible after the wound has formed. However fibrosis can develop over days or even weeks. Therefore the subject being treated may well benefit by administration of a compound (such as progesterone or tamoxifen) even if the composition is administered days or even weeks after the wound occurred or the disorder developed (or was diagnosed).

When used as a prophylactic (e.g. before surgery or when there is a risk of developing a fibrotic disorder) the compositions should be administered as soon as the risk of undesirable fibrosis or a potential for a poor rate of wound healing has been recognised (as may be the case in elderly subjects). For instance, a cream or ointment containing 17 β-oestradiol may be applied to a site on the skin of subject where elective surgery is to be performed and an increased rate of wound healing is subsequently desired. In this case, the composition may be applied during the preoperative preparation of the subject or it may even be desirable to apply the composition in the hours or days preceding the surgery (depending upon the health status and age of subject as well as the size of the wound to be formed).

Frequency of administration will depend upon the biological half-life of the compound used. Typically a cream or ointment containing a compound should be administered to a target tissue such that the concentration of the compound at the wound site or tissue affected by a fibrotic disorder is maintained at a level suitable for having a therapeutic effect. This may require administration daily or even several times daily. In the case of the use of 17 β-oestradiol for wound healing, we have found that administration of the compound (by a patch applied to the wound) for 24 hours post-wounding is sufficient to improve the rate at which the wound heals.

Known procedures, such as those conventionally employed by the pharmaceutical industry (e.g. in vivo experimentation, clinical trials etc), may be used to establish specific formulations of compositions and precise therapeutic regimes (such as daily doses of the compounds and the frequency of administration).

Generally, compositions in accordance with the invention will contain 0.001% to 4% by weight of the compound which influences the sex hormone system. Purely by way of example a composition containing between 0.005% and 1% by weight of oestriol, oestradiol, ethinyloestradiol or testosterone is suitable for application to an existing (i.e. "open") wound.

By way of further example, a composition which is to be used preoperatively as a prophylactic may contain between 0.01% and 2% by weight of oestriol, oestradiol, ethinyloestradiol or testosterone to have the desired effect on wound healing.

A preferred composition for use in the present invention comprises a maximum of 1% (e.g. between 0.005% and 1%) to 17 β-Oestradiol.

A suitable daily dose of a compound which influences the sex hormone system will depend upon the factors discussed above as well as upon the size of the wound to be treated. Typically the amount of a compound required for the treatment of wounds or fibrotic disorders will be within the range of 1 ng to 100 g of the active compound/24 hours depending upon the size of the wound or extent of fibrosis amongst several other factors. By way of example 0.5–500 $\mu$g/24 hrs of 17 β-oestradiol is a suitable dose for treating a wound (to increase the rate of healing) made by a 4 mm punch biopsy of the skin, more preferably 10–100 $\mu$g/24 hrs of 17 β-oestradiol is used and most preferably 25 $\mu$g/24 hrs of 17 β-oestradiol is used.

A preferred means of using protein or peptide compounds which influence the sex hormone system is to deliver the compound to the wound by means of gene therapy. For instance gene therapy could be used to increase expression of peptide ligands for chorionic gonadotrophin receptors, follicle stimulating hormone receptors or luteinising hormone receptors. Alternatively gene therapy may be used to modulate the expression of an enzyme involved in the synthesis of steroid sex hormones (e.g. oestrogens, androgens or progesterone). Therefore according to a fourth aspect of the present invention there is provided a delivery system for use in a gene therapy technique, said delivery system comprising a DNA molecule encoding for a protein which directly or indirectly modulates wound healing and/or modulates fibrosis or scarring by influencing the sex hormone system, said DNA molecule being capable of being transcribed to lead to the expression of said protein.

According to a fifth aspect of the present invention there is provided the use of a delivery system as defined in the preceding paragraph for use in the manufacture of a medicament for use in wound healing and/or modulation of fibrosis or scarring.

According to a sixth aspect of the present invention there is provided a method of treating a wound and/or modulating fibrosis or scarring comprising administering to a patient in need of treatment a therapeutically effective amount of a delivery system as defined for the fourth aspect of the invention.

The delivery systems are highly suitable for achieving sustained levels of an active agent at a wound site or site of fibrosis over a longer period of time than is possible for most conventional delivery systems. Protein may be continuously expressed from cells at the wound site or site of fibrosis that have been transformed with the DNA molecule of the fourth aspect of the invention. Therefore, even if the protein has a very short half-life as an agent in vivo, therapeutically effective amounts of the protein may be continuously expressed from the treated tissue.

Furthermore, the delivery system of the invention may be used to provide the DNA molecule (and thereby the protein which is an active therapeutic agent) without the need to use conventional pharmaceutical vehicles such as those required in ointments or creams that are contacted with the wound. This is particularly beneficial as it can often be difficult to provide a satisfactory vehicle for a compound for use in wound healing (which are required to be non-inflammatory, biocompatible, bioresorbable and must not degrade or inactivate the active agent (in storage or in use)).

The delivery system is such that the DNA molecule is capable of being expressed (when the delivery system is administered to a patient) to produce a protein which directly or indirectly has activity for wound healing and/or treatment of fibrosis or scarring. By "directly" we mean that the product of gene expression per se has the required activity for wound healing and/or regulating fibrosis or scarring. By "indirectly" we mean that the product of gene expression undergoes or mediates (e.g. as an enzyme) at least one further reaction to provide an agent effective for wound healing and/or regulating fibrosis or scarring.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors can be designed such that the vector will autonomously replicate in the nucleus of the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the wound, fibrosis or scarring has been treated or prevented).

The delivery system may provide the DNA molecule to the subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to the wounded area topically or by injection.

The protein expressed from the DNA molecule may be one which directly or indirectly provides for wound healing with reduced scarring, one which provides an increase in the rate of wound healing whilst possibly resulting in increased scar formation or one which serves to regulate (inhibit, prevent or reverse) fibrosis.

Whilst the above considerations mainly apply to wounds and fibrotic disorders of man it will be appreciated that wound healing, scarring and fibrosis can also be problematic in other animals (especially domestic animals such as horses, dogs, cats etc). For instance abdominal wounds or adhesions are a major reason for having to put down horses, as are tendon and ligament damage leading to scarring or fibrosis. The compounds, compositions and delivery systems discussed above are suitable for use in the healing of such animals.

BRIEF DESCRIPTION OF THE DRAWINGS

The present invention will now be further described with reference to the following non-limiting Examples and accompanying drawings in which.

EXAMPLE 1

Experiments were performed in which the effect of ovariectomy (and thus the removal of oestrogens) had on wound healing.

1.1 Methods 1.1.1 Preparation of Rats

Female Sprague Dawley rats were housed together in three groups (1A, 1B and 1C) of nine to allow for synchro nised oestrus cycling. Group 1A were ovariectomised (OVX) 18 days prior to wounding to allow circulating sex hormone levels to be eliminated. Group 1B (control) were untreated and Group 1C had the same operative procedure as the OVX (Group 1A), but without the removal of the ovaries, to ensure that the OVX operative procedure had no effect on the wounding studies (sham).

1.1.2 Treatments

17 β-oestradiol (Sigma) was prepared as sterile 0.1% and 1% solutions in phosphate buffered saline (PBS) containing 0.1% and 1% 2-hydroxypropyl-β-cyclodextrin respectively, 2-hydroxypropyl-β-cyclodextrin is used in preparations as a carrier molecule to increase the water solubility of β-oestradiol. PBS/cyclodextrin was used as a vehicle control.

Animals from Groups 1A, 1B and 1C were given 4×1 cm length full thickness incisional wounds at 4.5–5.5 cm and 7.5–8.5 cm below the base of the skull, 1 cm either side of the midline. A single 100 μl intradermal injection was then given at each of the four wound sites. Each of the wounds (a total of 36 wounds on 9 rats in each group) received either 100 μl of oestradiol (0.1% or 1%), 100 μl of vehicle control (0.1% or 1% cyclodextrin) or was left unmanipulated (no injection).

1.1.3 Tests at Day 7 Post-wounding

The wounds were allowed to heal for 7 days after which the wounded tissue was excised for histological analysis.

7 μm paraffin-embedded sections were stained with H&E and Masson's Trichrome. The rate of re-epithelialisation (at day 7 post-wounding), and wound sizes as determined by planimetry, were determined with image analysis using an Olympus Vanox camera and PC image capture system. Collagen quantity within the wound was determined by two observers blinded to the identity of the specimen.

1.2 Results (7 Days Post-wounding)

Unmanipulated sham group (Group 1C) and control group wounds (Group 1B) had re-epithelialised, were cellular and had laid down new collagen. Unmanipulated ovariectomised group (OVX; Group 1A) wounds showed delayed re-epithelialisation, were very wide and cellular in comparison to sham/control group wounds (1B and 1C) and had laid down very little new collagen. This indicated that OVX causes a delay in the rate of wound healing at 7 days post wounding (see Table 1).

Cyclodextrin (vehicle controls) has an adverse effect on the wounds at the highest dose of 1%. In all three groups the wounds were wide and cellular with little new collagen. These effects were not noticeable with 0.1% cyclodextrin, where wounds were similar to control PBS wounds which had fewer cells and had laid down some new collagen.

All wounds treated with 1% β-oestradiol had re-epithelialised and laid down new collagen. OVX group wounds were narrower than control/sham group wounds, indicating that they had an increased rate of wound healing compared to control PBS treated and unmanipulated wounds. They all had a lot of new collagen, very few inflammatory cells and were very narrow. In the OVX 0.1% β-oestradiol treated wounds, a single application of 0.1% β-oestradiol was able to overcome the adverse effects of the cyclodextrin vehicle and OVX, to show accelerated wound healing compared to control wounds. These findings correlate with human wound data which show an acceleration of wound healing at early time points when post-menopausal women are taking oestrogen and progesterone HRT.

There were differences between the two doses of β-oestradiol with the 0.1% β-oestradiol showing better results than the 1% β-oestradiol. This may be as a result of the adverse effects of the cyclodextrin vehicle since it is present at 1% in the 1% β-oestradiol solution and at 0.1% in the 0.1% β-oestradiol solution.

These findings indicate that an optimum dose of β-oestradiol is less than 1% (particularly when cyclodextrin is used as a carrier), and using a different vehicle, different doses and different times of administration may result in an even greater acceleration of wound healing.

In FIG. 1, sections were stained with Mallory's Trichrome a=day 7 wound in an intact female rat (1B); b=day 7 wound in an OVX rat (1A) (note delayed re-epithelialisation and reduced collagen deposition and a significant increase in wound width); c=day 7 wound from an intact female treated with 5 mm oestrogen; d=day 7 wound in an OVX rat (note improved wound healing in c and d with large quantities of mature collagen within a narrow wound and complete re-epithelialisation). Scale bar=100 μm.

TABLE I

| TREATMENT | GROUP | EPITHELIALISATION | WOUND WIDTH | NEW COLLAGEN | CELLS |
|---|---|---|---|---|---|
| UNMANIPULATED | OVX | delayed | very wide | + | +++ |
|  | SHAM | Y | average | ++ | ++ |
| 1% CYCLODEXTRIN (vehicle) | OVX | delayed | wide | ++ | +++ |
|  | SHAM | Y | wide | + | +++ |
| 0.1% CYCLODEXTRIN (vehicle) | OVX | Y | average | ++ | + |
|  | SHAM | Y | average | ++ | ++ |
| 1% OESTRADIOL (with 1% cyclodextrin vehicle) | OVX | Y | narrow | +++ | ++ |
|  | SHAM | Y | wide | ++ | ++ |
| 0.1% OESTRADIOL (with 0.1% cyclodextrin vehicle) | OVX | Y | narrow | ++++ | + |
|  | SHAM | Y | narrow | +++ | ++ |

Y = epithelialised,
+ = little/few,
++++ = lots)

EXAMPLE 2

The effect of Hormone Replacement therapy (i.e. oestrogen supplementation) on wound healing in post-menopausal women was examined to demonstrate how compounds that influence the sex hormone system are able to modulate wound healing.

2.1 Methods
2.1.1 Patients

Approval for this study was given by the local Ethics (Committee, Twenty health-status defined post-menopausal women aged 55 to 63 years were split into two groups:

(i) GROUP 2A comprised ten subjects who were taking no medication except for Hormone Replacement Therapy (HRT) (mean age 55.9 yr, SD 2.92; oestrogen patch and oral progesterone combination for greater than 3 months).

(ii) GROUP 2B comprised ten subjects who were taking no medication, and had never taken HRT (aged group: mean age 59.5 yr, SD 4.28).

In addition, ten young health-status defined females, aged 20–39 years (GROUP 2C: mean age 29.8 yr, SD 5.03) who were taking no medication (including the oral contraceptive pill) formed a third group for study.

All subjects had normal medical histories and examinations, CXR, ECG, haematological, lipid and biochemical profiles. Subjects were all non-smokers, with normal dietary histories and body mass indices.

2.1.2 Biopsies

After informed consent, subjects from each of Groups 2A, 2B and 2C underwent two 4 mm punch biopsies from the upper inner arm (a non sun-exposed site) following local infiltration with 1 ml 1% lignocaine. Each biopsy of normal skin was bisected and one-half embedded in Optimal Cutting Temperature compound (Miles Inc. Elkhart, Ind.), frozen over liquid nitrogen and stored at −70° C., and one-half snap-frozen in liquid nitrogen and stored at −70° C.

The wounds were covered with a Multisorb dry gauze dressing (Smith & Nephew, UK) for 24 hours and then left uncovered.

2.1.3 Re-biopsy

Five subjects from Groups 2A, 2B and 2C underwent re-excision of the wounds at day 7 post-wounding, and the other five subjects at day 84 post-wounding.

The left upper inner arm was cleaned with isopropyl alcohol, elliptical excisions of the wounds were made following 1% lignocaine infiltration and two sutures were used to close the gap. Each wound was bisected and processed as described above (2.1.2).

2.1.4 Study of Biopsies

Some biopsies were used for molecular analysis, Microdissection of these wounds was undertaken to ensure that there was no contamination from normal skin.

2.1.4.1 Immunostaining

7 $\mu$m cryosections were prepared and immunostained using a TGF-$\beta$1 antibody (BDA19: R&D systems, Oxfordshire) to test for the presence of TGF-$\beta$1 in the wound.

2.1.4.2 Image Analysis and Scarring Assessment of Wounds

The rate of re-epithelialisation (at day 7 post-wounding only) was determined with image analysis using a Joyce Loebel Mini-magiscan. The macroscopic appearance of the healing human wounds stained with Masson's Trichrome was scored using the following system:

a) Colour—(compared to surrounding skin) 1=Perfect; 2=Minor mismatch; 3=Obvious mismatch; 4=Gross mismatch.

b) Contour 1=Normal; 2=Palpable; 3=Hypertrophic; 4=Keloid.

c) Texture 1=Same as normal skin; 2=Proud/indented; 3=Firm; 4=Hard.

The microscopic appearance of healing wounds was assessed using the following scoring system:

a) Collagen orientation (separate assessments for upper-papillary and deep-reticular dermal levels of the wound): 1=Normal basket-weave; 2=Basket-weave>Parallel fibres; 3=Parallel>Basket-weave fibres; 4=Parallel fibres.

b) Bundle density (separate assessments for upper-papillary and deep-reticular wound): 1=All bundles normal; 2=>50% bundles normal; 3=<50% bundles normal; 4=All bundles abnormal (increased or decreased density);

c) Rete ridge formation: 1=Normal appearance; 2=Reduced numbers; 3=None.

2.1.5 Fibroblast Experiments in Vitro

Fibroblasts were extracted from the first biopsy samples of Groups 2A, 2B and 2C and cultured in order to measure TGF-$\beta$ expression from the cells.

2.1.5.1 Cell Culture

Human dermal fibroblasts were explanted from the 4 mm punch biopsy specimens of normal skin. Fibroblasts used in the study were cultured at 37° C. in 95% air; 5% $CO_2$ at 100% relative humidity, in phenol red-free DMEM (Gibco), 100 U/ml penicillin, 100 mg/ml streptomycin, 1 mM sodium pyruvate, 2 mM L-glutamine, non-essential amino acids and charcoal-stripped 10% FCS (Gibco, UK) (to remove endogenous steroids).

2.1.5.2 Treatment of Fibroblasts

Cultured cells at passage 3–5 were seeded overnight in 24-well plates at a density of $2\times10^5$ cells per well in serum free media. The following morning oestrogen or progesterone (made soluble by the incorporation of the carrier cyclodextrin; Sigma, Poole), ranging from 1 pM to 1 mM doses, were added to the medium for 24 hrs. All samples were assessed in triplicate. The media was removed after the 24 hr incubation. 1 mg/ml of aprotinin, leupeptin and pepstatin A was then added to the media which was used immediately in a TGF-$\beta$ assay (see below). Controls included cyclodextrin at the appropriate concentration, and serum-free medium alone.

2.1.5.3 Assesment of Fibroblast Proliferation

The cells were then incubated with [$^3$H] thymidine in serum-free medium (0.5 $\mu$Ci/well) to assess the effect of oestrogen or progesterone on fibroblast proliferation. After 24 hrs, the thymidine solution was aspirated and replaced by 10% TCA for 4 hrs at 4° C. The TCA was replaced by 250 $\mu$ls 1M NaOH solution for 18 hrs. Two 100 $\mu$l aliquots from each well were measured for radioactivity in a scintillation counter. In parallel experiments, the effect of hormones/controls on protein synthesis was investigated by the addition of 20 $\mu$g/ml cycloheximde (to inhibit protein translation) for 15 mins prior to the 24 hr incubation period.

2.1.5.4 TGF-$\beta$ Assay

TGF-$\beta$ levels in the media (2.1.5.2) were determined using a mink lung growth inhibition assay as described by Danielpour et al, (J Cell Physiol, 138 p79–86) Briefly, mink lung epithelial cells (MLECs) were maintained in DMEM and 10% FCS at 37° C. in 10% $CO_2$. Subconfluent cells were trypsinized, resuspended in 10% FCS, pelleted at 500 g for 5 min, washed with 10 ml of assay buffer (DMEM, 2% FCS, 10 mM HEPES pH 7.4, penicillin 25 U/ml, streptomycin 25 $\mu$g/ml), resuspended in assay buffer and seeded at $10^5$ cells/well in a 24-well Costar plate. After 1 hr conditioned media or control media (with varying concentrations of hormones ranging from 1 pM-1 mM or cyclodextrin alone) were added, 22 hrs later cells were pulsed with [$^3$H] thymidine (0.5 $\mu$Ci/well) for 2 hrs at 37° C., and the procedure described above for the extraction and measurement of radioactivity followed (2.1.5.3). A standard curve was produced using 10–1000 pg/ml TGF-$\beta$ standard (R&D) from which inhibition data could be converted to pg/ml. Results were presented as pg/ml TGF-$\beta$/10$^5$ cells (relative to control valves for each individual hormone concentration).

2.1.6 Quantitative RT-PCR

Quantitative RT-PCR was used to determine the steady-state levels of TGF-$\beta$1 mRNA in the acute wound and in 10$^5$ cells from the fibroblast in vitro studies (2.1.5) Cellular RNA was isolated from specimens using the method of Chomcynski and Sacchi (Anal, Biochem, 162 p156–159 (1987)). Purity of extraction was assessed using the A$_{260/280}$ ratio spectrophotometrically, which in all cases was above 1.75. No significant difference were observed in total RNA content/$\mu$g wet weight tissue between individuals at each time-point. Quantitative RT-PCR was performed as described by Tarnuzzer et al. (Biotechniques 20 p670–674 (1996)) Briefly, the reverse transcriptase reaction was carried out using 8 decreasing dilutions of template with 1 $\mu$g of authentic cellular RNA. $\beta$-actin was used as a positive control. PCR reactions were carried out on the reverse transcription reaction. Electrophoresis was then carried out on a 2% agarose gel containing 25 ng/ml ethidium bromide at 100 v for 1 hr using an Electro 4 tank (Hybaid, Teddington, UK) and photographed using a dual intensity transilluminator (Genetic Research instrumentation, Dunmow (UK) with a Polaroid MP 4+ camera and 665 Polaroid Black and White film, Photographic images were captured using a PC Image Software system (Foster Finley, Newcastle, UK) on a 486 DX2 Dan computer (Dan, UK) and a CCD camera (Swift, UK). The band intensities were determined by image analysis using a Macintosh computer and NIH software programme. Band intensity values were normalised based on the molecular weights of the products. The log of the ratio of band intensities within each lane was plotted against the log of the copy number of template added per reaction. Quantities of target messages were determined where the ratio of template and target band intensities were equal to 1. Copy numbers were expressed per total RNA (for wound tissue) or expressed per cell (for in vitro studies). The latter were calculated by assuming 26 pg RNA/cell.

2.1.7 Statistical Analysis

All data are presented as mean +/−SD. All data follow a normal distribution. Differences between means were evaluated by independent Student t-test where appropriate and by one-factor and multiple ANOVA (analysis of variance) complemented by Tukey-HSD test. In all circumstances $p<0.05$ was considered to be significant.

Figure 1A:
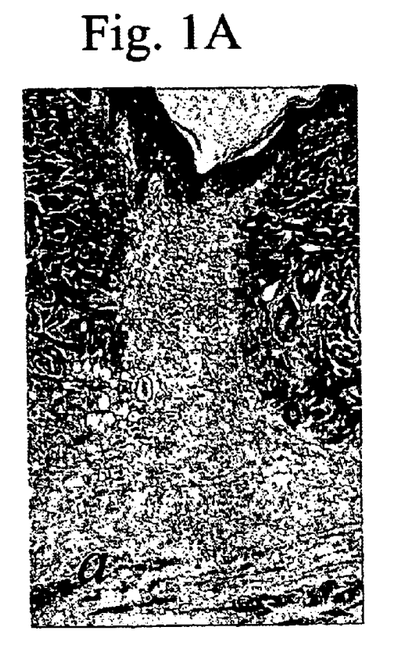
FIG. 1 represents photographs of stained histological sections of wounds from rats in Example 1.
Figure 1B:
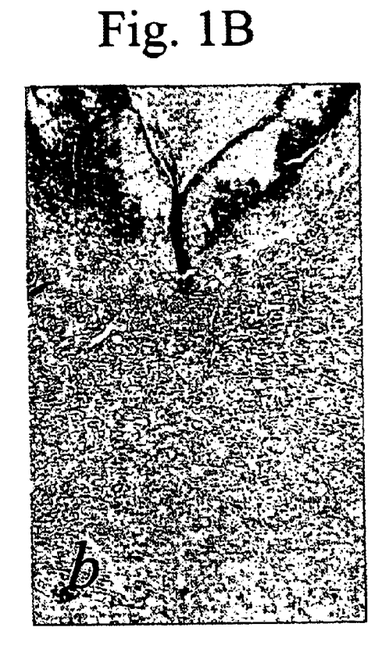
Figure 1C:
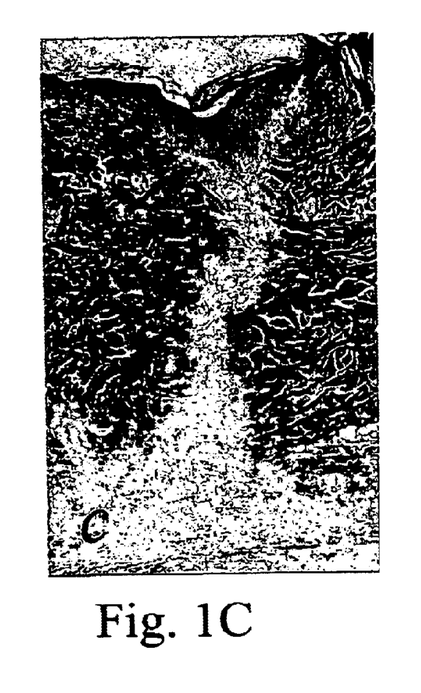
Figure 1D:
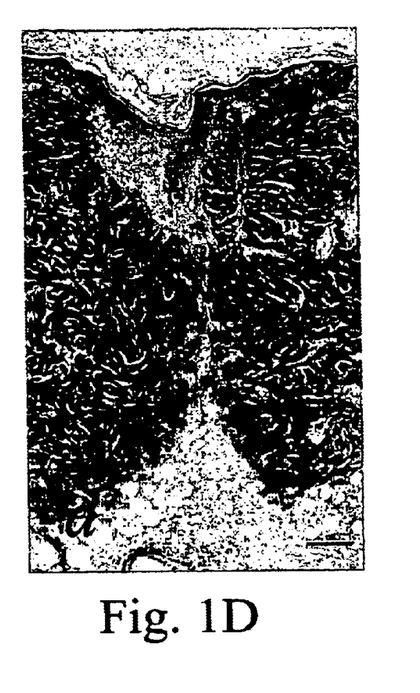
Figure 2:
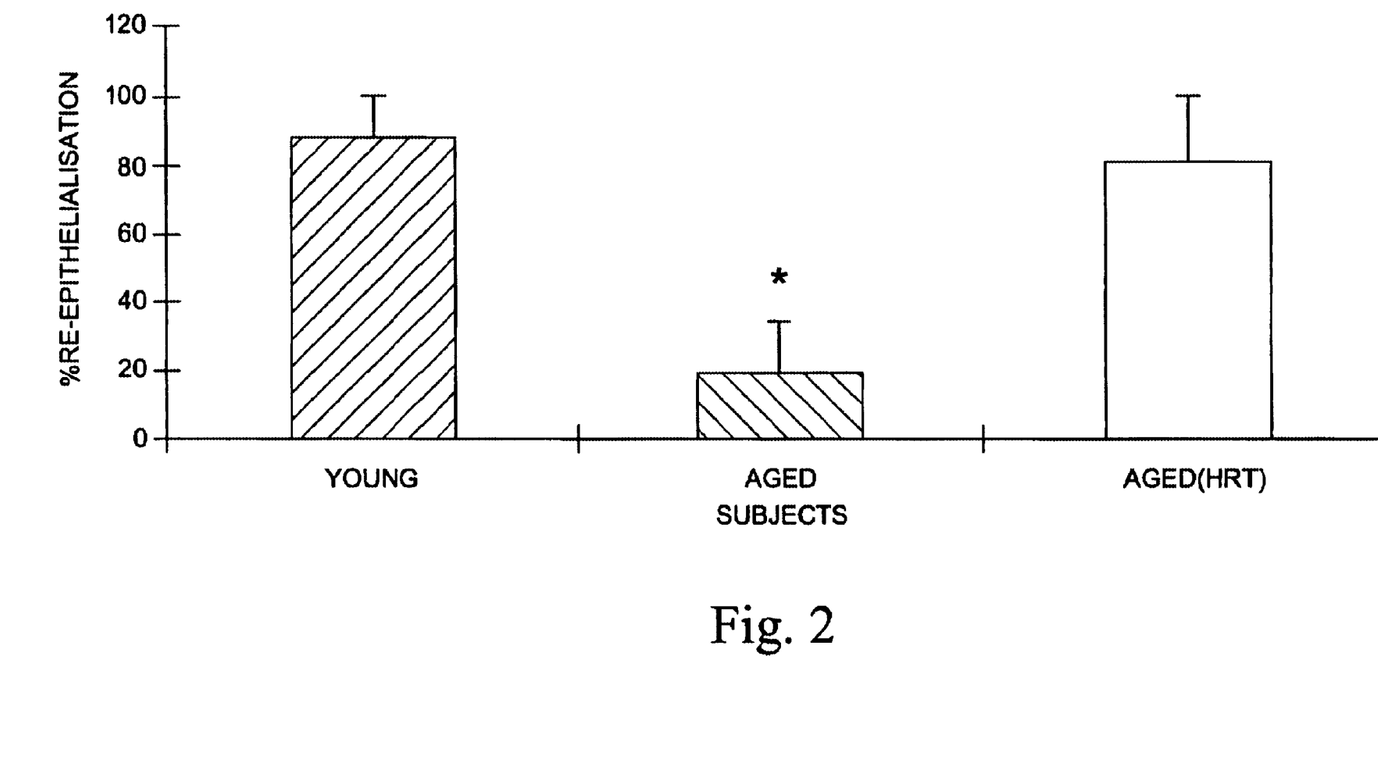
FIG. 2 is a graph representing the rate of re-epithelialisation at day 7 post-wounding in the subjects of Example 2.

2.2 Results 2.2.1 The Effects of Age and Circulating Sex Steroids on Human Wound Repair 2.2.1.1 Rate of Healing: Re-epithelialisation and Collagen Deposition Intrinsic ageing (Group 2B) was associated with a delay in the rate of wound healing in terms of re-epithelialisation at day 7 post-wounding (FIG. 2), and reduced matrix collagen deposition at days 7 and 84. However, the HRT group (2A) showed a marked acceleration of the rate of re-epithelialisation at day 7, similar to that observed in the young group (2C) (FIG. 2). Moreover, the HRT group had markedly increased levels of collagen deposition (which approached the levels observed in the young group, 2C) at days 7 and 84 compared to the aged group.

Figure 3A:
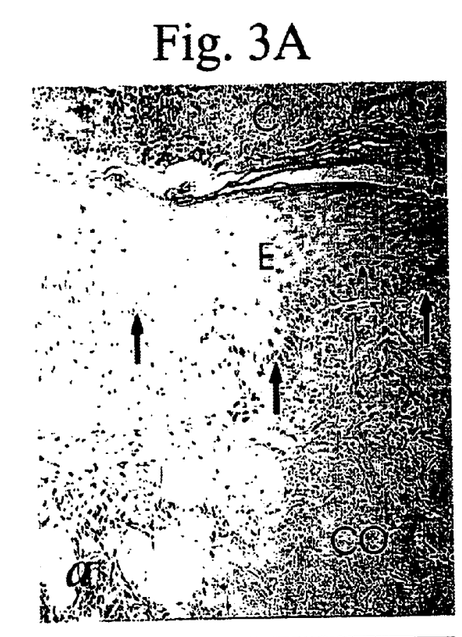
FIG. 3 represents photographs of histological sections of wounds stained with H&E for subjects of Example 2.
Figure 3B:
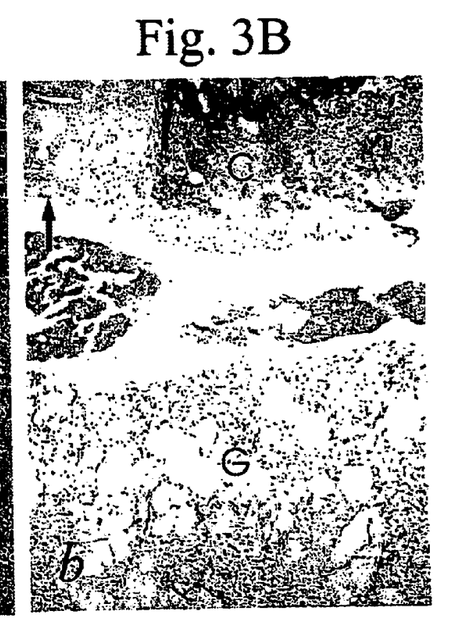
Figure 3C:
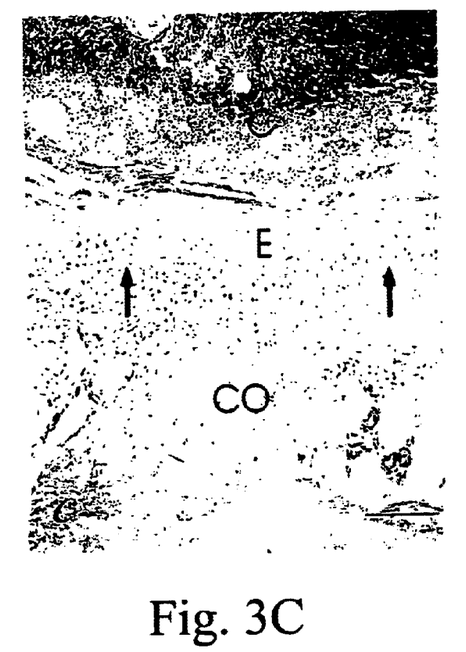

FIG. 3 represents a histological sections of wounds stained with H&E for a=28 year old (group 2C), b=57 yr old (group 2B) and c=58 yr old on HRT (group 2A). The H&E staining shows collagen deposition (CO) in the wounds of groups 2A and 2C (c and a) In b (group 2B) the granulation tissue (G) is immature with absent staining for collagen. Re-epithelialisation is complete in a (2C) and c (2A) with neo-epidermis (E) completely covering the wound (arrows indicating the basal layer of the epidermis). In b the arrow points to the migrating neo-epidermis which is present only at the wound edge. C=clot. Scale bar=100 $\mu$m.

2.2.1.2 Quality of Healing: Degree of Microscopic and Macroscopic Scarring

The macroscopic appearance of mature scar tissue was significantly superior in the aged subjects (Groups 2A and 2B) in terms of colour, texture and contour, in contrast to hypertrophic scarring in the young subjects (2C) (scores with n=5 for each group: young (2C) mean=10 SD=1: aged (2B) mean=4 SD=2; HRT (2A) mean=10 SD=2; $p<0.001$). The scars of the aged group (2B) were consistently pale and flat, compared to the pigmented, everted lesions in the young group (2C). Increasing age was also a significant factor in determining the quality of microscopic repair, with restoration of the dermal architecture in the wounds of the aged group (scores young (2C) mean=13 SD=2; aged (2B) mean=9 SD=2; HRT (2A) mean=13 SD=2; $p<0.01$). Notably, in the wounds of the aged subjects rete ridges had regenerated, large papillary blood vessels were observed, and the basket-weave organisation of the collagen resembled that of normal dermis. In the wounds of the young (2C), the dermo-epidermal junction was flat, and densely packed parallel layers of collagen were present throughout the wound. HRT (2A) was associated with similar adverse scarring profiles both microscopically and macroscopically to those of young females. Microscopically, the dermo-epidermal junction was flat, and the dermis consisted of parallel layers of scar tissue collagen and fibroblasts. Macroscopically, the wounds were invariably raised and pigmented.

2.2.1.3 TGF-$\beta$1 Immunostaining and mRNA Levels

Figure 4A:
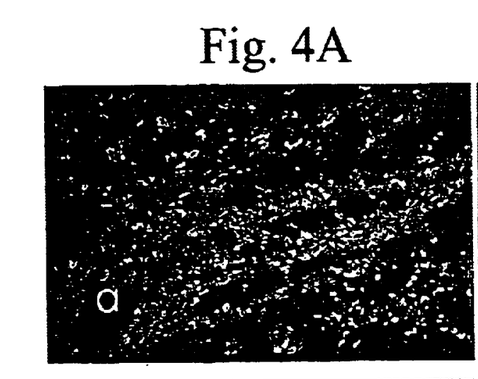
FIG. 4 represents immunostaining for wound samples in Example 2.
Figure 4B:
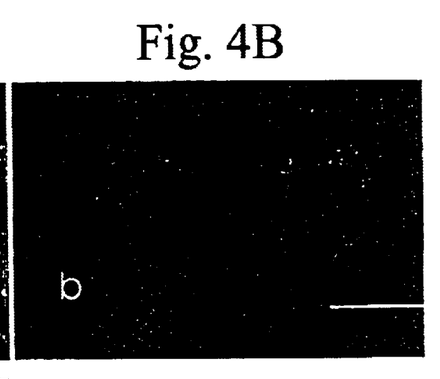
Figure 4C:
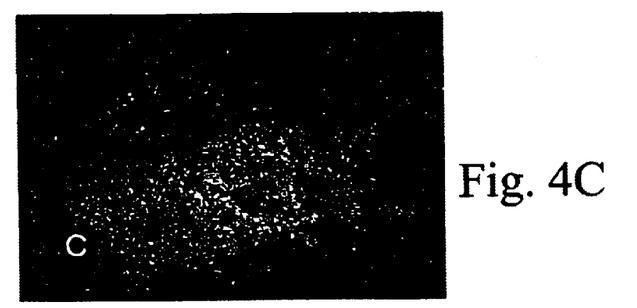

Wound TGF-$\beta$1 levels were markedly and consistently decreased in the aged group (2B) at day 7 post-wounding compared to both the young group (2C) and to the HRT group (2A) as illustrated in FIG. 4 in which staining for TGF-$\beta$1 is shown for a=22 year old (group 2C), b=60 yr old (group 2B) and c=61 yr old on HRT (group 2A).

The quantitative RT-PCR data indicated that intrinsic ageing in females of group 2B was associated with low levels of steady-state mRNA for TGF-$\beta$1 with a mean of 87 copies/pg total RNA (SD of 6) at day 7 post-wounding and a mean of 116 copies/pg total RNA (SD) of 9) at day 84, whereas for the young group (2C) the mean copy number/pg total RNA was 5656 (SD of 74) at day 7, decreasing to 140 copies/pg (SD of 9) at day 84. For the HRT group (2A) the mean levels were 6216 copies/pg (SD of 97) at day 7, declining to 140 copies/pg total RNA (SD of 9) at day 84.

Figure 5A:
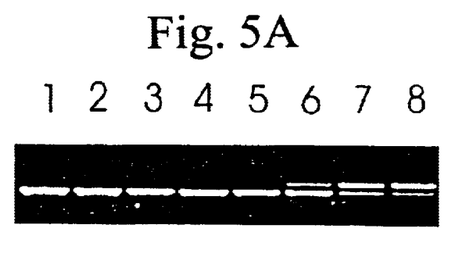
FIG. 5 represents TGF-$\beta$1 mRNA levels at day 7 post-wounding in the subjects of Example 2.
Figure 5B:
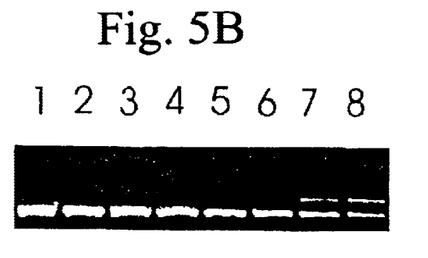
Figure 5C:
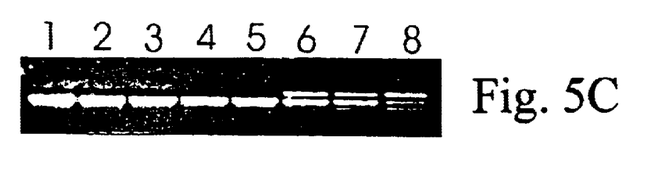

The differences between mRNA levels at day 7 between the different groups is illustrated in FIG. 5. In FIG. 5, the mRNA from a=22 year old (group 2C), b=60 yr old (group 2B) and c=61 yr old on HRT (group 2A) are shown. Differences in mRNA between the aged group (2B) and the young (2C) or the HRT group (2A) were highly significant (p=0.006). Thus, HRT reverses the age-related decrease in local TGF-$\beta$1 mRNA steady-state levels observed during early wound healing. This suggests that compounds which influence the sex hormone system may be doing so by a mechanism which involves modulation of TGF-$\beta$ expression.

2.2.1.4 The Effect of HRT on Macrophage Numbers

Immunostaining for a monocyte/macrophage marker revealed that HRT (2A) was associated with an increase in macrophage numbers in the day 7 wounds with a mean of 39 cells/field area (SD of 6). This was similar in degree to the numbers of macrophages observed in the wounds of young females (2C): mean of 35 cells/field area (SD of 4). The wounds of the aged group (2B) had significantly reduced numbers of macrophages compared to the other two groups with a mean of 12 cells/field area (SD of 4) (one-factor ANOVA F (2.14)=14.3, p=0.0007, Turkey-HSD range for 0.05 level =3.77). The increased macrophage infiltration observed in the wounds of the HRT group compared to the aged group may have important consequences for the wound healing process: in addition to their role in phagocytosis, macrophages also produce a variety of cytokines, including TGF-$\beta$1, which is important in stimulating cell migration, proliferation and matrix production.

2.2.3 Effects of Oestrogen and Progesterone on Human Dermal Fibroblast Proliferation and TGF-$\beta$1 Production To further investigate the effects of compounds which influence the sex hormone system on wound healing we determined the effects of oestrogen and progesterone separately on fibroblast proliferation and TGF-$\beta$ production. Mean baseline fibroblast proliferation after 24 hrs (media only) was not significantly different between the three groups.

Figure 6:
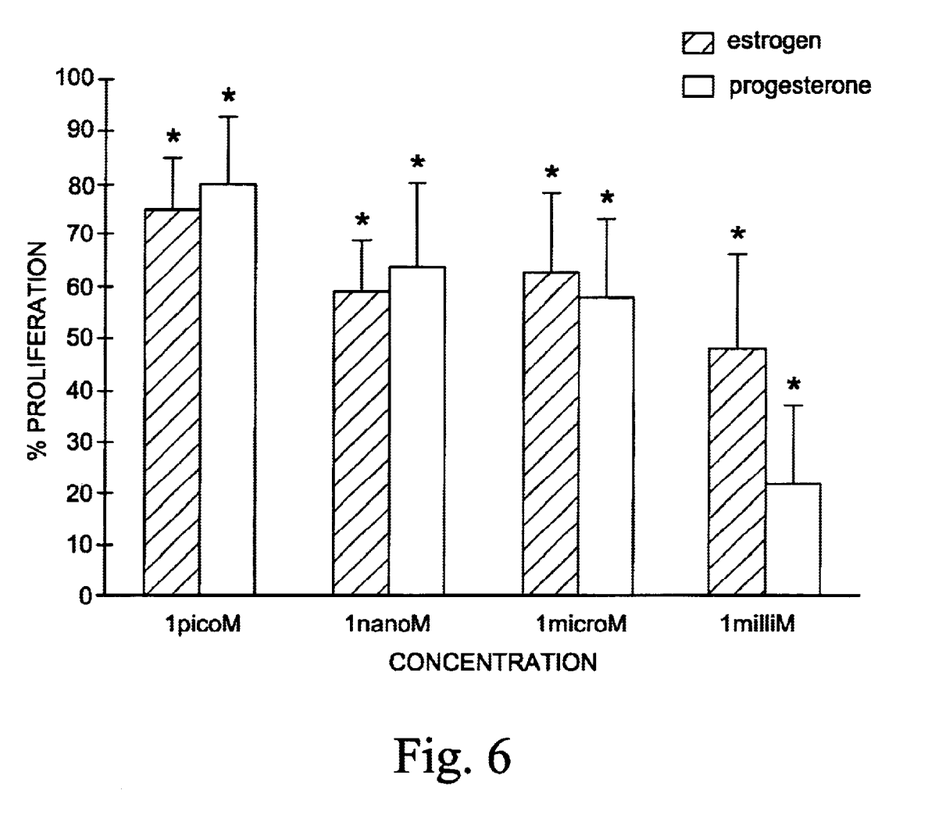
FIG. 6 is a graph representing the effect of oestrogen on human fibroblast proliferation in fibroblast derived from the subjects of Example 2.

Oestrogen at doses ranging from 1 pM to 1 mM inhibited the proliferation of fibroblasts from both young and aged subjects (compared to cyclodextrin controls) (FIG. 6). The degree of inhibition of proliferation was similar for fibroblasts from both young and aged females. Progesterone inhibited fibroblast proliferation at doses of 1 pM to 1 mM in all subjects, and to a significantly greater degree than oestrogen at 1 mM (p<0.05).

Cell viability was not affected by hormone treatment as determined by the Trypan Blue exclusion test. Pre-incubation of media for 30 mins with a neutralising antibody to TGF-$\beta$1 (10 $\mu$g/l; R&D systems) prior to addition to the cells did not reverse the hormone effect, indicating that the inhibition of proliferation occurred independently of TGF-$\beta$1.

Using the mink lung cell assay (2.1.5.2), conditioned media from baseline control fibroblast cultures from young female subjects (Group 2C) treated only with serum-free media (without hormones or cyclodextrin carrier) exhibited significantly greater inhibition of mink lung epithelial cell (MLEC) proliferation compared to old female fibroblasts (Groups 2A or 2B) (p<0.05; Table II). Pre-incubation of media for 30 mins with a neutralising antibody to TGF-$\beta$1 prior to addition to the MLECs completely reversed the hormone effect, indicating that the inhibition of MLEC proliferation was dependent upon TGF-$\beta$1.

When fibroblasts were incubated with oestrogen or progesterone, conditioned media induced growth inhibition of MLECs dependent upon the hormone in question, and its concentration (relative to controls) (Table II). Neutralising antibody to TGF-$\beta$1 (at 10 $\mu$g/ml, R&D) abolished the effects of the hormones at all concentrations assessed when pre-incubated with samples for 30 mins prior to addition to the mink lung cells (antibodies to TFG-$\beta$2 and $\beta$3 had no effect). Antibodies at this concentration added to mink lung cells (in control media) had no effect on thymidine uptake compared to control media alone. Total TGF-$\beta$1 levels in the heat-activated conditioned media were increased following 24 hr of oestrogen treatment in all subjects tested, with a maximal increase of TGF-$\beta$1 at the mM oestrogen dose (compared to controls), with a 4-fold mean increase in levels for young cells (2C), and a 12-fold increase for cells from aged subjects (2A and 2B) (Table II). Progesterone treatment of fibroblasts had no significant effect on TGF-$\beta$1 production (compared to controls) for young fibroblasts (Group 2C), however there was a significant 2-fold increase in levels at the nM and $\mu$M doses for the fibroblasts from the aged subjects (2A or 2B). There was no increase in active TGF-$\beta$1 after either oestrogen or progesterone treatment (i.e. non-heat-activated samples had no effect on the mink lung cell assay compared to the appropriate control). These data suggest that oestrogen is the major sex steroid involved in dermal fibroblast production/secretion of TGF-$\beta$1 and that the mechanism by which compounds that influence the sex hormone system exert their effect on wound healing may be by modulation of TGF-$\beta$1 levels.

TABLE II

TGF-$\beta$1 levels secreted by young (2C) and old female (2A or 2B) dermal fibroblasts as determined by the Mink lung cell growth inhibition assay.

| CELL TYPE | TREATMENT | TGF-beta LEVELS (pg/ml/$10^5$ cell/24 hr) | FOLD INDUCTION |
|---|---|---|---|
| YOUNG FEMALE | CONTROL (media alone) | 108 ± 26 | |
| | pM Oestrogen | 118 ± 24 | 1 |
| | nM Oestrogen | 312 ± 30 | 3* |
| | $\mu$M Oestrogen | 282 ± 22 | 2.6* |
| | mM Oestrogen | 428 ± 58 | 4* |
| | pM Progesterone | 70 ± 31 | 0.6 |
| | nM Progesterone | 115 ± 20 | 1 |
| | $\mu$M Progesterone | 96 ± 13 | 1 |
| | mM Progesterone | 82 ± 13 | 0.8 |
| OLD FEMALE | CONTROL (media alone) | 34 ± 11 | |
| | pM Oestrogen | 80 ± 50 | 2.4* |
| | nM Oestrogen | 280 ± 60 | 8.3* |
| | $\mu$M Oestrogen | 315 ± 47 | 9.3* |
| | mM Oestrogen | 416 ± 80 | 12.2* |
| | pM Progesterone | 32 ± 13 | 1 |
| | nM Progesterone | 90 ± 38 | 2.6* |
| | $\mu$M Progesterone | 65 ± 15 | 2* |
| | mM Progesterone | 33 ± 13 | 1 |

To distinguish between transcriptional and post-transcriptional control of TGF-$\beta$1 levels, we determined the mRNA steady-state levels of fibroblasts treated with varying concentrations of oestrogen. No significant differences in TGF-$\beta$1 mRNA levels were found between control and treated fibroblasts from all females (regardless of age) (Table III). Cycloheximide added in conjunction with the hormones or media alone had no effect on total TGF-$\beta$1 protein levels observed, indicating that inhibiting protein synthesis had no effect on the raised levels of TGF-$\beta$1 in the media following oestrogen treatment. Cycloheximide had no effect on cell viability at the dose used in the study. The data suggest that the increase in total cytokine levels in the media secondary to oestrogen treatment was due to post-translational events.

TABLE III

Effects of age and hormone treatment on dermal fibroblast TGF-$\beta$1 mRNA levels as determined by quantitative RT-PCR

| CELL TYPE | TREATMENT | TGF-beta mRNA LEVELS (copies/cell) |
|---|---|---|
| YOUNG FEMALE (2C) | CONTROL (media alone) | 1200 ± 158 |
| | pM Oestrogen | 1190 ± 300 |
| | nM Oestrogen | 1300 ± 272 |
| | $\mu$M Oestrogen | 1180 ± 130 |
| | mM Oestrogen | 1250 ± 188 |
| | pM Progesterone | 1130 ± 254 |
| | nM Progesterone | 1145 ± 206 |
| | $\mu$M Progesterone | 1090 ± 280 |
| | mM Progesterone | 1100 ± 310 |

TABLE III-continued

Effects of age and hormone treatment on dermal fibroblast TGF-β1 mRNA levels as determined by quantitative RT-PCR

| CELL TYPE | TREATMENT | TGF-beta mRNA LEVELS (copies/cell) |
|---|---|---|
| OLD FEMALE (2A or 2B) | CONTROL (media alone) | 1080 ± 160 |
| | pM Oestrogen | 1155 ± 215 |
| | nM Oestrogen | 1100 ± 370 |
| | µM Oestrogen | 1100 ± 235 |
| | mM Oestrogen | 990 ± 325 |
| | pM Progesterone | 950 ± 210 |
| | nM Progesterone | 1000 ± 275 |
| | µM Progesterone | 1110 ± 290 |
| | mM Progesterone | 1300 ± 430 |

EXAMPLE 3

Experiments were conducted to illustrate the effect of topical oestrogens on the wound healing in a clinical trial using men and women.

3.1 Methods 3.1.1 Patients

Approval for this study was given by the local Ethics Committee. Forty health-status defined volunteers split into four groups:

(i) GROUP 3A comprised ten women with mean age 76.3 yr (Sd 5.6) who received oestrogen supplements (25 µg/24 hrs of oestradiol)
(ii) GROUP 3B comprised ten women with mean age 72.5 yr (Sd 7.1) who received placebo instead of oestrogen.
(iii) GROUP 3C comprised ten men with mean age 69.6 yr (Sd 3.6) who received oestrogen supplements
(ii) GROUP 3D comprised ten men with mean age 71.8 yr (Sd 8.9) who received placebo instead of oestrogen.

All subjects had normal medical histories and examinations. CXR. ECG. haematological, lipid and biochemical profiles. Subjects were all non-smokers, with normal dietary histories and body mass indices.

3.1.2 Biopsies

After informed consent subjects from each of Groups 3A, 3B, 3C and 3D underwent two 4 mm punch biopsies from the upper inner arm (a non sun-exposed site) following local infiltration with 1 ml 1% lignocaine. Each biopsy of normal skin was bisected and one-half embedded in Optimal Cutting Temperature compound (Miles Inc. Elkhart, Ind.), frozen over liquid nitrogen, and stored at −70° C., and one-half snap-frozen in liquid nitrogen and stored at −70° C.

The area for biopsy was covered by a 2×3 cm patch (placebo Groups 3B and 3D or active oestradiol 3A and 3C) through which the biopsies were made. The patch was covered by a Multisorb dry gauze dressing (Smith & Nephew) and both were removed after 24 hrs. The active patches contained sufficient oestradiol such that the wound sites were exposed to 25 µg/24 hrs of oestradiol.

3.1.3 Re-biopsy

Five subjects from Groups 3A, 3B, 3C and 3D underwent re-excision of the wounds at day 7 post-wounding, and the other five subjects from each group at day 84 post-wounding.

The left upper inner arm was cleaned with isopropyl alcohol, elliptical excisions of the wounds were made following 1% lignocaine infiltration and two sutures were used to close the gap. Each wound was bisected and processed as described above (3.1.3).

3.1.4 Measurements of Endogenous Hormones

Circulating oestrogen levels in the female groups (3A and 3B) were <50 pmol/l with progesterone <2 nmol/l both at initial biopsy and at re-excision.

For the male groups (3C and 3D) all progesterone levels were <2 nmol/l. For Group 3C: testosterone levels were 15.9 nmol/l (Sd 3.9). SHBG was 47.3 (SD 14.2) and oestrogen levels 92 pmol/l (Sd 16.6). For Group 3D: testosterone levels were 13.0 nmol/l (Sd 3.5). SHBG was 46.9 (SD 27.4) and oestrogen levels 100 pmol/l (Sd 14.7). Prolactin levels and PSA levels (3C and 3D) were within normal limits.

3.1.5 Study of Biopsies

Some biopsies were used for molecular analysis and micro-dissection of the wound was undertaken to ensure that there was no contamination from normal skin.

3.1.5.1 Image Analysis of Wounds

7 µm paraffin-embedded sections were strained with H&E and Masson's Trichrome. The rate of re-epithelialisation (at day 7 post-wounding), and wound sizes as determined by planimetry, were determined with image analysis using an Olympus Vanox camera and PC image capture system. Collagen quantity within the wound was determined by two observers blinded to the identity of the specimen on the following scale +=minimal quantities; ++=less than normal skin; +++=similar to normal skin; ++++=greater than normal skin.

3.1.5.2 Dimensional Analysis System

The wound stiffness at day 80 was determined using the non-disruptive Dimensional Analysis System (Das). Previous studies have correlated wound breaking strength values (ultimate pressure at failure) to wound stiffness using this system. The system applies a multiaxial load (negative pressure) to the wound and measures the deformation due to the load of two reflective targets placed at the wound edges, using a high resolution camera and video processor. Pressure was applied to a maximum of 100 mmHg and then released, Stiffness was measured between 20 and 80 mmHg.

3.1.5.3 Fibronectin Zymography

Proteases responsible for fibronectin degradation were identified by zymography using fibronectin-containing acrylamide gels (12% acrylamide and 0.33 mg/ml fibronectin, Central Blood Products Ltd). Tissue samples were lyophilized and homogenized using a ground glass homogenizer containing 0.5 ml buffer (100 mM Tris/HCl, 6M Urea, 15 mM $CaCl_2$, 0.25% Triton-X100, pH 7.4). After centrifugation at 11,000 rpm for 10 min at 4° C. samples (20 µg dry wt) were incubated for 30 min at 37° C. with 2× Laemmli sample buffer and subjected to electrophoresis under non-reducing conditions (Laemmli, 1970). After electrophoresis, the gels were washed twice with 2.5% Triton-X100 for 1 hr to remove SDS. The gels were briefly washed with double distilled water and incubated for 18 h at 37° C. in developing buffer containing 50 mM Tris/HCl, 150 mM NaCl and 5 mM $CaCl_2$, pH 7.4. At the end of incubation the gels were stained with 0.5% Coomassie brilliant blue and destained. Areas of protease activity appeared as clear zones against a dark blue background. Duplicate gels were incubated with either the addition of 10 mM metalloprotease inhibitor. EDTA (BDH, Poole) or 1.7 mM serine protease inhibitor, aminoethylbenzenesulfonylfluoride (AEBSF; Sigma). Broad range pre-stained molecular weight standards (Bio-rad) were used as molecular weight markers. Separate lanes were loaded with 500 ng and 50 ng of human neutrophil elastase (ICN).

3.1.5.4 SDS-PAGE and Immunoblotting

Protein samples (20 µg dry wt) extracted as described above were subjected to electrophoresis on a 12% acrylamide gel. Parallel fibronectin zymograms were run simultaneously. For immunoblotting, polypeptides were transferred to nitrocellulose paper (0.45 μm pore size. Bio-Rad) by electrophoresis at 20V for 30 min (Bio-Rad Semi dry transfer blot apparatus) in transfer buffer (25 mM Tris/HCl, 192 mM glycine, 10% methanol, pH 8.3). To block non-specific binding, immunoblots were incubated in 4% Marvel low-fat milk in TBST (10 mM Tris/HCl, 150 mM NaCl, 0.5% Tween-20 pH 7.5) for 18 hours at 4° C. The transferred proteins were incubated with polyclonal anti-human neutrophil elastase antibody (Calibiochem Co) diluted 1:500 in TBST for 2 hours at room temperature with shaking, followed by incubation with horseradish peroxidase conjugated goat anti-rabbit IgG (Sigma) at 1:3000 dilution in TBST with 4% non-fat milk for 1 hour at room temperature. Antibody binding was visualized using the ECL kit according to manufacturer's instructions (Amersham Int.).

3.1.5.5 Elastase Determination

Tissue samples (20 μg dry wt) and human neutrophil elastase (0.01–0.3 μg/ml) were incubated for up to 1 h at 37° C. in 200 μl of 0.1M Hepes buffer, pH 7.5, containing 0.5M NaCl, 10% dimethylsulfoxide and 0.1 mM elastase substrate (methoxysuccinyl-ala-ala-pro-val-p-nitroanilide; Calibiochem Co;). Substrate degradation was determined by measuring $OD_{410}$ (Dynatech MR5000). A standard curve for degradation was prepared from the elastase data. Results were expressed as ng/ml elastase activity/20 μg dry wt.

3.1.6 Statistical Analysis

All data are normalised and assessed using an independent student t-test. P<0.05 is considered significant.

3.2 Results 3.2.1 The Effect of Oestrogen on the Rate of Wound Healing

Oestrogen treatment accelerated the rate of re-epithelialization in both female (3A) and male subjects (3C) relative to placebo controls (3B and 3D respectively) (see Table IV). The results were only significant in the female group (p>0.005) because of a discrepancy between the sexes in the placebo group (males re-epithelialized more quickly than females). Wound area at day 7 post-wounding had significantly reduced with oestrogen treatment in both male Groups 3C and 3D (p<0.05). Collagen levels were consistently increased both at day 7 and day 80 post-wounding in both sexes treated with oestrogen (3A and 3C) compared to placebo (3B and 3D). Wound stiffness was not affected by oestrogen treatment at day 80 post-wounding.

3.2.2 The Effect of Oestrogen on Wound Elastase Activity

Tissue extracts from day 7 acute wounds all degraded fibronectin showing a major band at approximately 30 kd, but consistently less degradation occurred in the oestrogen-treated groups (3A and 3C). The 30 kd fibronectin-specific protease activity in all the samples was abolished by incubation with the broad range serine protease inhibitor. AEBSF, but not by the metalloprotease inhibitor. EDTA, suggesting the major fibronectin degradation activity was due to a serine protease, which co-migrated with commercial neutrophil elastase. Immunoblotting confirmed the 30 kd protease activity seen on fibronectin zymograms was elastase. Elastase activity was present only in placebo-treated groups (3B and 3D). Elastase activity was quantified using a synthetic elastase substrate degradation assay, which showed that oestrogen treatment significantly reduced elastase activity in day 7 wounds compared to placebo (<50 ng elastase per 20 μg dry wt of tissue for the placebo groups concurring with the Western blot data). (Table IV).

TABLE IV

Topical oestrogen accelerates wound healing in elderly males and females.

| | FEMALES | | MALES | |
| --- | --- | --- | --- | --- |
| | PLACEBO (3B) | OESTROGEN (3A) | PLACEBO (3D) | OESTROGEN (3C) |
| Wound area | 1408.7 (19) | 1204 (49)* | 1461 (28) | 1173 (61)* |
| % Rate of re-epithelialisation | 3.3 (3.3) | 74.5 (10.5)* | 30 (16.9) | 62.5 (21.7) |
| Collagen Quantities DAY 7 | + | ++ | + | ++ |
| DAY 80 | +++ | ++++ | +++ | ++++ |

3.2.3 The Effect of Oestrogen on Scarring

Figure 7:
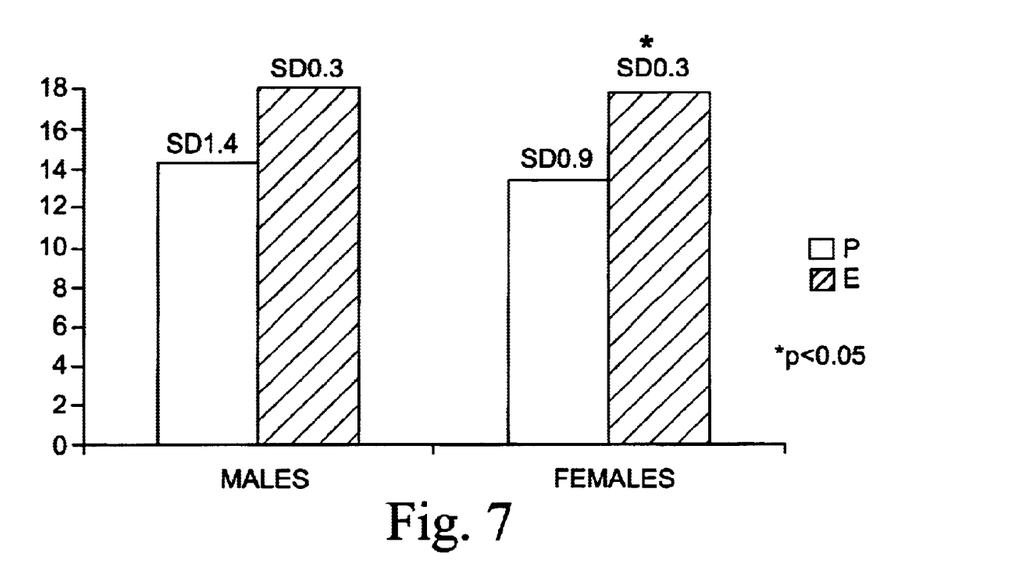
FIG. 7 is a graph representing the effect of oestrogen and progesterone on scar formation evaluated microscopically in Example 3.
Figure 8:
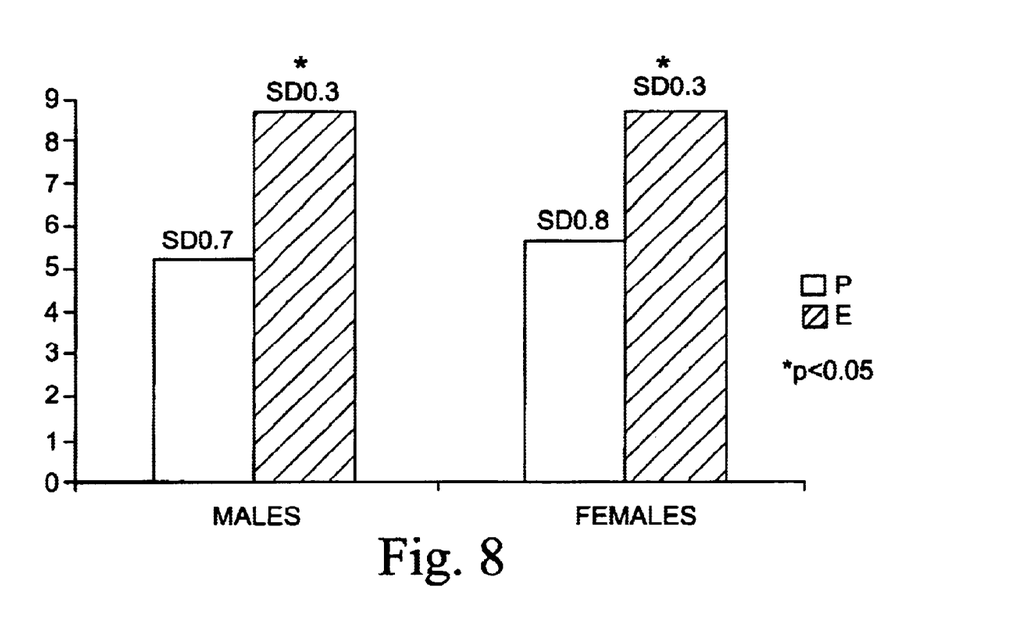
FIG. 8 is a graph representing the effect of oestrogen and progesterone on scar formation evaluated macroscopically in Example 3.

FIGS. 7 and 8 illustrate the effect of oestrogen (e) on scarring (microscopically and macroscopically respectively) as determined in 2.1.4.2. Oestrogen treatment was associated with an inferior quality of wound (which may be correlated with TGF-β levels). This indicates that an oestrogen antagonist is associated with a superior quality of scar (and decreased TGF-β levels) and may be used according to the second embodiment of the invention to treat or prevent scarring and/or fibrotic disorders.

FIGS. 7 and 8 also show that progesterone treatment (p) is associated with superior scaring and therefore progesterone is a suitable compound for use according to the second embodiment of the invention.

What is claimed is:

1. A method of promoting re-epithelialization of wounds of the skin comprising administering to a person in need thereof a compound that promotes oestrogenic activity in an amount sufficient to promote said re-epithelialization.

2. The method as claimed in claim 1 wherein said compound is an oestrogen or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone and a phytoestrogen.

3. The method as claimed in claim 1 wherein said compound is an oestrogen hormone.

4. The method as claimed in claim 3 wherein said compound is 17β-oestradiol.

5. The method as claimed in claim 4 wherein said compound is administered in a composition comprising between 0.01% and 4% 17β-oestradiol.

6. The method according to claim 1 wherein the wound is an acute wound.

7. The method according to claim 6 wherein the wound is a penetrative injury, a burn or the result of elective surgery.

8. The method according to claim 1 wherein the wound is a chronic wound.

9. The method according to claim 8 wherein the wound is a diabetic, venous or decubitus ulceration.

* * * * *